(12) United States Patent
Gilbert et al.

(10) Patent No.: US 6,221,874 B1
(45) Date of Patent: Apr. 24, 2001

(54) METHOD OF TREATING BONE LOSS BY STIMULATION OF CALCITONIN

(75) Inventors: Adam Matthew Gilbert, Congers; Gerardo Francisco, Orangeburg, both of NY (US); Magda Asselin, Mahwah, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/303,972

(22) Filed: May 3, 1999

Related U.S. Application Data

(60) Provisional application No. 60/135,497, filed on May 8, 1998.

(51) Int. Cl.[7] .................... C07D 473/06; C07D 473/08; A61K 31/522; A61P 3/14; A61P 19/10
(52) U.S. Cl. .................. 514/263; 514/265; 544/267; 544/269; 544/270; 544/271; 544/272
(58) Field of Search .................... 544/267, 272, 544/269, 271, 220; 514/263, 265

(56) References Cited

U.S. PATENT DOCUMENTS

| | | | |
|---|---|---|---|
| 3,900,474 | * | 8/1975 | Ginger .................... 544/272 |
| 5,409,934 | * | 4/1995 | Smith .................... 544/272 |

OTHER PUBLICATIONS

Lau–Cam, J. Liquid Chromagraphy 14(10) 1939, Oct. 1991.*
Bilezikian, J.P., Fert. Menopausal Studies, 41, 148–155 (1996).
Rico, H. et al., Calcif, Tissue Int. 56, 181–185 (1995).
Buckle et al., J. Med. Chem., 37, 476–485 (1994).
Primenko et al., Ukr. Khim. Zh (Russ. Ed.) 51, 660–663 (1985) and Translation.
Acatrinei et al., An. Stint Univ. Al I. Cuza: Iasi, Sect. 2a, 20, 247–252 (1974) and Translation.

* cited by examiner

Primary Examiner—Mark L. Berch
(74) Attorney, Agent, or Firm—Rebecca R. Barrett

(57) ABSTRACT

Compounds of the formula

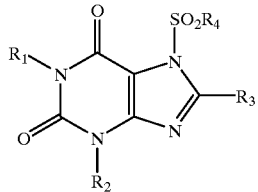

$R_1$ and $R_2$ are independently alkyl of 1 to 6 carbon atoms, allyl, or substituted allyl of 3 to 6 carbon atoms; $R_3$ is hydrogen, alkyl of 1 to 6 carbon atoms, or cycloalkyl of 3 to 10 carbon atoms; and $R_4$ is phenyl or naphthyl substituted with alkyl of 1 to 6 carbon atoms, alkoxy of 1 to 6 carbon atoms or $NR_5R_6$; substituted or unsubstituted phenylalkyl wherein the alkyl group contains 1 to 6 carbon atoms; substituted or unsubstituted 5 to 10 membered heteroaryl having 1 to 3 heteroatoms selected from N, S and O; substituted or unsubstituted cycloalkyl of 3 to 10 carbon atoms; or substituted or unsubstituted cycloalkylalkyl of 4 to 10 carbon atoms; provided that phenyl or naphthyl is substituted with $NR_5R_6$ when $R_1$ and R2 is alkyl, are useful in the treatment of various disorders associated bone loss by increased transcription and elevation of plasma calcitonin levels. Such disorders include, but are not limited to: Paget's Disease, post menopausal osteoporosis, senile osteoporosis, and glucocorticoid-induced osteoporosis.

14 Claims, No Drawings

METHOD OF TREATING BONE LOSS BY STIMULATION OF CALCITONIN

This application claims the benefit of U.S. Provisional Application No. 60/135,497, which was converted from U.S. patent application Ser. No. 09/074,675, filed May 8, 1998.

BACKGROUND OF INVENTION

Calcitonin is a 32 amino acid polypeptide hormone secreted by the parafollicular or C cells of the thyroid gland in response to elevated blood levels of calcium. This hormone decreases blood calcium (hypocalcemic activity) primarily by inhibiting bone resorption through plasma membrane-associated receptors on the osteoclast. High-turnover bone loss, as seen with hypercalcemia of malignancy, estrogen withdrawal as following the onset of the menopause, and certain anti-inflammatory or arthritis therapies, has recently been shown to be preventable by the administration of calcitonin (Bilezikian, J. P., *J. Fert. Menopausal Studies*. 1996, 41, 148–155). As recently demonstrated for post-menopausal osteoporosis, treatment leads to not only a maintenance of bone mass and total body calcium, but also to decreases in the incidence of hip and vertebral fractures [Rico, H., et al., *Calcif. Tissue Int*. 1995, 56, 181–185, Gennari, C., *Aust. Family Physician*. 1994, 48, 196–200. Thus, it is apparent that calcitonin is an appropriate therapeutic for the prevention and treatment of osteoporosis by virtue of its hypocalcemic activity.

Although calcitonin has demonstrated efficacy in the prevention of high-turnover bone loss, a limitation for its wide-spread use is the lack of oral bioavailability, necessitating administration by parental (intra-muscular) or nasal routes. However, stimulation of endogenous calcitonin synthesis and release by inducer compounds would be expected to result in a similar therapeutic effect. This invention describes the ability of a series of xanthine sulfonamides to induce the expression and release of endogenous calcitonin, an activity not previously described for these compound.

Smith et al. disclose a class of 6-aminoxanthine-7-sulfonamides, 6-amino-sulfonylxanthine-7-sulfonamides and 6-aminobis(sulfonyl)xanthine-7-sulfonamides as phosphodiesterase (PDE) inhibitors in U.S. Pat. No. 5,409,934 and *J. Med. Chem*. 1994, 37, 476–85. Ginger et al. disclose of series a xanthine-7-sulfonamides as bronchodilating agents in U.S. Pat. No. 3,900,474.

The synthesis of variously substituted xanthine sulfonamides are described in the following publications: Buckle et al., *J. Med. Chem*. 1994, 37, 476–85, Primenko et al., *Ukr. Khim. Zh*. (*Russ. Ed*.) 1985, 51, 660–3, Acatrinei et al, *An. Stint. Univ. "Al. I Cuza" Iasi, Sect*. 2a, 1974, 20, 247–52.

DESCRIPTION OF THE INVENTION

The present invention relates to xanthine sulfonamides having pharmacological activity, and to their use in the treatment of disorders associated bone loss by increased transcription and elevation of plasma calcitonin levels. Such disorders include, but are not limited to: Paget's Disease, post menopausal osteoporosis, senile osteoporosis, and glucocorticoid-induced osteoporosis.

In accordance with this invention there, is provided a group of compounds represented by the formula (I):

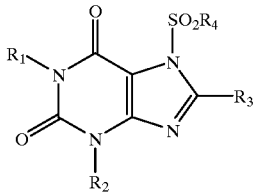

(I)

wherein:

$R_1$ and $R_2$ are independently, alkyl of 1 to 12 carbon atoms, alkenyl of 2 to 12 carbon atoms, allyl of 3 to 12 carbon atoms, cycloalkyl of 3 to 10 carbon atoms, aryl of 4 to 10 carbon atoms, 4 to 10 membered heteroaryl or a moiety of the formula $(CH_2)_m$—A wherein m is an integer from 1 to 9 and A is cycloalkyl of 3 to 7 carbon atoms;

$R_3$ is H, alkyl of 1 to 12 carbon atoms or cycloalkyl of 3 to 10 carbon atoms; and $R_4$ is alkyl of 1 to 12 carbon atoms, cycloalkyl of 3 to 10 carbon atoms, cycloalkylalkyl of 4 to 10 carbon atoms, aryl of 4 to 10 carbon atoms, aralkyl of 5 to 10 carbon atoms; or 4 to 10 membered heteroaryl having 1 to 3 heteroatoms selected from N, S and O;

or a pharmaceutically acceptable salt thereof.

In some preferred aspects of the invention are provided compounds of formula (I):

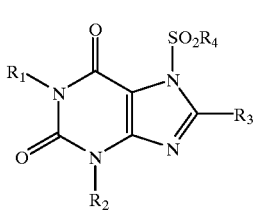

(I)

wherein:

$R_1$ and $R_2$ are independently alkyl of 1 to 6 carbon atoms or allyl of 3 to 6 carbon atoms;

$R_3$ is hydrogen, alkyl of 1 to 6 carbon atoms, or cycloalkyl of 3 to 10 carbon atoms;

$R_4$ is aryl of 4 to 10 carbon atoms substituted with halogen, alkyl of 1 to 6 carbon atoms, alkoxy of 1 to 6 carbon atoms or $NR_5R_6$; substituted or unsubstituted aralkyl of 7 to 10 carbon atoms; substituted or unsubstituted 4 to 10 membered heteroaryl having 1 to 3 heteroatoms selected from N, S and O; substituted or unsubstituted cycloalkyl of 3 to 10 carbon atoms; or substituted or unsubstituted cycloalkylalkyl of 4 to 10 carbon atoms; provided that aryl is substituted with $NR_5R_6$ when $R_1$ and $R_2$ are alkyl;

$R_5$ and $R_6$ are independently selected from H, —OH, —$COR_7$, —$OCOR_7$; provided that $R_5$ and $R_6$ are not both H; and $R_7$ is alkyl of 1 to 6 carbon atoms; or a pharmaceutical salt thereof.

In still other preferred aspects of the invention:

$R_1$ and $R_2$ are independently alkyl of 1 to 6 carbon atoms;

$R_3$ is H; and $R_4$ is 4 to 6 membered heteroaryl.

In yet other preferred aspects of the invention:

$R_1$ and $R_2$ are independently alkyl of 1 to 6 carbon atoms;
$R_3$ is H;
$R_4$ is aryl substituted with $NR_5R_6$.

In other preferred aspects of the invention $R_1$ or $R_2$ is allyl.

In still other preferred aspects of the invention, $R_4$ is cycloalkylalkyl of 6 to 10 carbon atoms or aralkyl of 5 to 10 carbon atoms.

Alkyl, whether used alone or as part of another group (i.e. alkoxy) refers to an aliphatic hydrocarbon group. Alkyl includes straight and branched chain alkyl groups containing from 1 to 12 carbon atoms, and more preferably 1 to 6 carbon atoms. For example, methyl, ethyl, propyl, isopropyl, butyl and t-butyl are encompassed by the term alkyl. In some embodiments of the present invention alkyl may refer to substituted or unsubstituted alkyl.

Alkenyl as used herein refers to an aliphatic hydrocarbon group containing a carbon-carbon double bond. Alkenyl includes straight and branched chain alkenyl groups containing from 2 to 12 carbon atoms, and more preferably from 2 to 6 carbon atoms. For example, ethenyl, n-butenyl, i-butenyl and n-pentenyl are encompassed by the term.

Allyl, as used herein refers to a conjugated hydrocarbon group containing from 3 to 12 carbon atoms, and more preferably from 3 to 6 carbon atoms. Allyl groups may be substituted or unsubstituted.

Halogen, as used herein means chlorine, bromine, iodine and fluorine.

Aryl, as used herein refers to single or multiple 4 to 10 membered aromatic ring radicals including but not limited to phenyl, naphthalene, anthracene, phenanthrene, indene and indacene. Preferred are phenyl and napthalene. In some embodiments of the present invention the aryl group may be substituted.

Aralkyl, as used herein refers to an aryl-alkyl group in which the aryl and alkyl are as previously described. Exemplary aralkyl groups include benzyl and phenethyl.

Heteroaryl as used herein refers to single or multiple 4 to 10 membered aromatic ring radicals having from 1 to 3 heteroatoms selected from S, O, or N including, but not limited to, furan, thiophene, pyrrole, imidazole, oxazole, thiazole, isoxazole, pyrazole, isoxazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine and isobenzofuran. Preferred hetroaryls include furan, thiophene, pyrrole, imidazole, oxazole, thiazole, isoxazole, pyrazole, isoxazole, isothiazole, oxadiazole, triazole, thiadiazole, quinolizine, quinoline, and isoquinoline. More preferred heteroaryls include furan, thiophene, imidazole, isoxazole, quinoline and pyrazole. In some embodiments of the present invention the heteroacryl group is substituted.

Throughout, carbon number refers to carbon backbone and does not include carbon atoms of substitutions such as alkoxy substitutions and the like.

Preferably, the substituted aryl group is substituted with from 1 to 4 groups and more preferable with 1 to 3 groups. The substituted heteroaryl group is preferably substituted with from 1 or 2 groups. Alkyl, alkenyl and cycloalkyl groups may also be substituted. Suitable substitutions include, but are not limited to halogen, alkyl, alkoxy, haloalkyl, haloalkoxy, hydroxy, hydroxyamino, alkylamino, nitro, nitrile, amino, cyano, oxy, carboxy alkoxycarbonyl, alkylcarbonyl, alkoxycarbonylalkyl, alkylcarbonyloxy and acetoxyacetamido.

The most preferred aspects of the present invention include:
  1,3-dibutyl-7-methanesulfonyl-3,7-dihydro-purine-2,6-dione;
  7-(butane-1-sulfonyl)-1,3-dibutyl-3,7-dihydro-purine-2,6-dione;
  1,3-dibutyl-7-(3-nitro-benzenesulfonyl)-3,7-dihydro-purine-2,6-dione;
  1,3-dibutyl-7-(3,4-dimethoxy-benzenesulfonyl)-3,7-dihydro-purine-2,6-dione;
  1,3-dibutyl-7-(thiophene-2-sulfonyl)-3,7-dihydro-purine-2,6-dione;
  1,3-dibutyl-7-(3-chloro-propane-1-sulfonyl)-3,7-dihydro-purine-2,6-dione;
  1,3-dibutyl-7-(naphthalene-1-sulfonyl)-3,7-dihydro-purine-2,6-dione;
  1,3-dibutyl-7-(4-hydroxya,ino-benzenesulfonyl)-3,7-dihydro-purine-2,6-dione;
  1,3-dibutyl-7-phenylmethanesulfonyl-3,7-dihydro-purine-2,6-dione;
  1,3-dibutyl-7-(7,7-dimethyl-2-oxo-bicyclo[2.2.1]hept-1-ylmethanesulfonyl)-3,7-dihydro-purine-2,6-dione;
  N-acetoxy-N-[4-(1,3-dibutyl-2,6-dioxo-1,2,3,6-tetrahydro-purine-7-sulfonyl)-phenyl]-acetamide;
  1,3-dibutyl-7-(2,4,6-trimethyl-benzenesulfonyl)-3,7-dihydro-purine-2,6-dione;
  1,3-dibutyl-7-(4-tert-butyl-benzenesulfonyl)-3,7-dihydro-purine-2,6-dione;
  1,3-dibutyl-7-(3,5-dimethyl-isoxazole-4-sulfonyl)-3,7-dihydro-purine-2,6-dione;
  3-butyl-1-(3-methyl-but-2-enyl)-7-(toluene4-sulfonyl)-3,7-dihydro-purine-2,6-dione;
  3-butyl-1-ethyl-7-(toluene-4-sulfonyl)-3,7-dihydro-purine-2,6-dione;
  3-butyl-7-(3,4-dimethoxy-benzenesulfonyl)-1-(3-methyl-but-2-enyl)-3,7-dihydro-purine-2,6-dione;
  1,3-dibutyl-7-(4-chloro-2,5-dimethyl-benzenesulfonyl)-3,7-dihydro-purine-2,6-dione;
  1,3-dibutyl-7-(3-chloro-propane-1-sulfonyl)-8-methyl-3,7-dihydro-purine-2,6-dione;
  1,3-dibutyl-8-methyl-7-(toluene-4-sulfonyl)-3,7-dihydro-purine-2,6-dione; or
pharmaceutical salts of the foregoing.

It is understood that the definition of the compounds of formula (I), when $R_1$, $R_2$ or $R_4$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques. The pharmaceutically acceptable salts are those derived from such organic and inorganic acids as: lactic, citric, acetic, tartaric, succinic, maleic, malonic, hydrochloric, hydrobromic, phosphoric, nitric, sulfuric, methanesulfonic, and similarly known acceptable acids. Where $R_1$, $R_2$ or $R_4$ contain a carboxyl group, salts of the compounds of this invention may be formed with bases such as alkali metals (Na, K, Li) or the alkaline earth metals (Ca or Mg).

As mentioned previously, the compounds of formula (I) have been found to increase transcription and elevate plasma levels of calcitonin. They are therefore useful in the treatment of disorders associated with high turnover bone loss, such as Paget's Disease, post menopausal osteoporosis, senile osteoporosis, and glucocorticoid-induced osteoporosis.

The present invention accordingly provides a pharmaceutical composition which comprises a compound of this invention in combination or association with a pharmaceutically acceptable carrier.

The compositions are preferably adapted for oral or subcutaneous administration. However, they may be adapted for other modes of administration.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents.

In accordance with the present invention, compounds of Formula (I) may be prepared such as described in U.S. Pat. No. 5,409,934, incorporated by reference herein.

The present invention further provides a compound of the invention for use as an active therapeutic substance. Compounds of formula (I) are of particular use in the increase of plasma calcitonin levels.

The present invention further provides a method of treating high turnover bone loss in mammals including man, which comprises administering to the afflicted mammal an effective amount of a compound or a pharmaceutical composition of the invention.

The following examples are presented to illustrate rather than limit the methods for production of representative compounds of the invention.

EXAMPLES

The plasma calcitonin elevation activity of the compounds of this invention was established in accordance with standard pharmaceutically accepted test procedures with representative compounds as follows:

Example A

Calcitonin/Luciferase Reporter Gene Expression Assay

This assay was used to determine the ability of a compound to stimulate transcription of a luciferase reporter gene regulated by 3 kb of the promoter region of the human calcitonin gene.

A reporter cell line (designated $C_{1-3}$) was developed by Oncogene Science by stable transfection of a single, unrearranged copy of a calcitonin/luciferase reporter gene construct into the TT human thyroid carcinoma cell line as described in U.S. Pat. No. 5,665,543. $C_{1-3}$ cells were plated at a density of 6,500–7,500 cells per well in a 96-plate microtiter plate. Twenty-four to forty-eight hours later, compounds were added to the wells in triplicate. Compounds were tested at a concentration of 10 µg/mL in 0.5% DMSO. Compounds that exhibited a transcription activation ratio (TAR)>1.5 (equivalent to >50% increase in transcription) advanced to primary follow-up (CA-FUP), in which compounds were re-screened at four concentrations: 10 µg/mL, 2 µg/mL, 0.4 µg/mL and 0.08 µg/mL. Controls were distributed throughout the plate, and include 1) unstimulated cells, for basal luciferase expression, 2) cells stimulated with 1 mM 8-CPT-cAMP (expect 2–3 fold induction).

The plates were incubated for 12 hours in a humidified $CO_2$ incubator, washed, and then lysed in luciferase assay buffer as described in U.S. Pat. No. 5,665,543, incorporated by reference herein in its entirety. The production of light is measured on a luminometer.

Calculations:

TAR Ratio: Stimulation of calcitonin promoter-dependent transcription is expressed as a ratio of luciferase activity (LUCI) in the presence of test compound compared to the LUCI activity in the untreated control:

$$\frac{LUCI \text{ test compound}}{LUCI \text{ control}} = TAR$$

Transcription Activity: Compounds are deemed active if TAR>1.5

The results of this study are shown in Table I.

TABLE I

Calcitonin Promoter/Luciferease Transcription Assay

| Compound | n | TAR (30 µM) |
|---|---|---|
| Example 1 | 2 | 2.1 |
| Example 2 | 2 | 2.2 |
| Example 3 | 3 | 2.0 |
| Example 4 | 3 | 2.5 |
| Example 5 | 2 | 1.8 |
| Example 6 | 3 | 2.0 |
| Example 7 | 3 | 2.5 |
| Example 8 | 3 | 2.0 |
| Example 9 | 3 | 2.3 |
| Example 10 | 3 | 2.0 |
| Example 11 | 3 | 2.1 |
| Example 12 | 2 | 2.1 |
| Example 13 | 2 | 1.8 |
| Example 14 | 2 | 2.5 |
| Example 15 | 3 | 2.1 |
| Example 16 | 3 | 2.1 |
| Example 17 | 3 | 2.8 |
| Example 18 | 3 | 2.5 |
| Example 19 | 2 | 1.7 |
| Example 20 | 2 | 2.0 |

Example B

Calcitonin Secretion/RIA Assay Protocol

This assay was used to determine the ability of a compound to increase the amount of calcitonin secreted by the $C_{1-3}$ cell line.

A calcitonin RIA kit (Nichols Institute Diagnostics, Kit# 40-2125) was used in accordance with manufacturer's suggestions as summarized below:

Materials:

Cell Line: $C_{1-3}$ (Parent Cell Line: TT-medullary thyroid carcinoma),

Reagents:

Reagent A - (Anti-Calcitonin)

Reagent B - ($^{125}$I-Calcitonin)

Regent C - (Anti-Goat Precipitant)

Regent D - (Zero Standard).

Reagents E-I - (Calcitonin Standards)

Reagents J-K (Calcitonin Controls: Level and Level 2)
Reagent L - (NSB Buffer)
Procedure:
1. Glass tubes were labeled to include Total Count (TC), Nonspecific Binding (NSB), Maximum Binding (Bo), Standards, Controls and Patient Sera in duplicate.
2. 300 mL of Standard Zero (Reagent D) was added to tubes 3 through 6 (NSB and Bo).
3. 300 mL of Standards* (Reagents E-1) was added to tubes 7–16 as follows:

| Tubes 7 & 8   | Standard E | 4 pg/mL  |
|---------------|------------|----------|
| Tubes 9 & 10  | Standard F | 10 pg/mL |
| Tubes 11 & 12 | Standard G | 20 pg/mL |
| Tubes 13 & 14 | Standard H | 40 pg/mL |
| Tubes 15 & 16 | Standard I | 80 pg/mL |

4. 300 mL of Patient Serum 1 was added to tubes 21 and 22, Patient Serum 2 was added to tubes 23 and 24, etc.
5. 100 mL of Reagent L (NSB Buffer) was added to tubes 3 and 4.
6. 100 mL of Reagent A (Anti-Calcitonin) was added to all tubes except tubes 1 & 2 (TC) and tube 3 & 4 (NSB). All tubes were vortexed, covered with parafilm or foil and incubated 44±6 hours at 2–8° C.
7. 100 mL of 125|Calcitonin (Reagent B) was added to all tubes. All tubes were vortexed, covered with parafilm or foil and incubated 22±3 hours at 2–8° C.
8. Reagent C (Anti-Goat Precipitant) was mixed gently but thoroughly by inverting the vial several times before use. 1 mL Reagent C was added to all tubes except 1 and 2 (TC). Tubes were vortexed and incubated 20 minutes at room temperature.
9. All tubes were centrifuged at 1300–1500×g for 15 minutes at 2–8° C.
10. Supernatant was decanted immediately after centrifugation taking care to leave the precipitate intact.
11. Tubes were counted 4 minutes or longer.
Calculations:

Secretion Ratio: Stimulation of calcitonin secretion is expressed as a ratio of secretion activity in the presence of test compound compared to the secretion activity in the untreated control:

$$\frac{\text{Secretion activity test compound}}{\text{Secretion activity control}} = \text{Secretion Ratio}$$

Secretion Activity: Compounds were designated active if Secretion Ratio>2.5.

TABLE II

Calcitonin Secretion/RIA Assay

| Compound | n | Secretion Ratio (30 μM) |
|---|---|---|
| Example 1 | 2 | 4.65 |
| Example 2 | 2 | 4.65 |
| Example 3 | 1 | 1.65 |
| Example 4 | 1 | 4.70 |
| Example 6 | 2 | 3.60 |
| Example 7 | 1 | 4.50 |
| Example 8 | 1 | 5.40 |
| Example 9 | 1 | 5.10 |
| Example 10 | 1 | 4.50 |
| Example 11 | 1 | 4.30 |
| Example 12 | 2 | 4.04 |
| Example 13 | 1 | 5.10 |
| Example 14 | 1 | 3.30 |
| Example 15 | 2 | 3.74 |
| Example 17 | 1 | 3.66 |
| Example 18 | 2 | 5.32 |
| Example 19 | 1 | 4.09 |
| Example 20 | 1 | 3.23 |

Example C

Serum Calcium/Plasma Calcitonin Determination Assay

This assay was used to evaluate the ability of a test compound to decrease serum calcium and increase plasma calcitonin in rats using either an acute or sub-acute protocol.

Acute Administration Study: After 72 hours acclimatization, young male or female Sprague Dawley rats weighing 170–250 g were randomly divided in groups of 8. The rats were fasted and given deionized $H_2O$ 18 hours prior to the start of the study. The purpose of the fasting is to reduce the variability in serum calcium and plasma calcitonin levels. Each rat is weighed.

The dosing regimen was as follows:

| Group | Treatment | Dose[b] | Route[c] |
|---|---|---|---|
| A | Vehicle (1% Tween 80 in saline) | 0.1 mL/100 g/day | ip or sc |
| B | Salmon Calcitonin | 5 IU/rat/day | sc |
| C–G | Test Compounds | 30 mg/kg/day | ip or sc |

[b]Single administration at time = 0
[c]sc administration is a single injection or is done continuously via a mini-pump At different intervals between 10 min and 6 h after dosing (usually 1 to 3 time points), 0.5 mL of blood was collected from each rat under ketamine/acepromazine anesthesia via the tail vein, subclavean artery, jugular vein or (terminal via) cardiac puncture. Serum was evaluated for total calcium and plasma was evaluated for calcitonin. After the final bleeding, the rats were euthanized humanely (by over exposure to $CO_2$).

Subacute Administration Study: After 72 hours acclimatization, young male or female Sprague Dawley rats weighing 170–250 g were randomly divided in groups of 8. The rats were fasted and given deionized $H_2O$ 18 hours prior to the start of the study. The purpose of the fasting is to reduce the variability in serum calcium and plasma calcitonin levels. Each rat was weighed.

The dosing regimen was as follows:

| Group | Treatment | Dose[b] | Route[c] |
|---|---|---|---|
| A | Vehicle (1% Tween 80 in saline, corn oil or $H_2O$) | 0.1 mL/100 g/2×/day | ip or sc |

-continued

| Group | Treatment | Dose[b] | Route[c] |
|---|---|---|---|
| B | Salmon Calcitonin | 5 IU/rat/day | sc |
| C–G | Test Compounds | 30 mg/kg/2×/day | ip or sc |

[b]In vehicle and test compound groups, the treatments that the animals received varied from one to twice a day and from time = 0 to time = 5 days. The rats are fasted and given deionized $H_2O$ 18 hours prior to the last administration of test compounds. The purpose of the fasting is to reduce the variability in serum calcium and plasma calcitonin levels.
[c]sc administration is a single injection or is done continuously via a mini-pump At different intervals between 10 min and 6 h after dosing (usually 1 to 3 time points), 0.5 mL of blood was collected from each rat under ketamine/acepromazine anesthesia via the tail vein, subclavean artery, jugular vein or (terminal via) cardiac puncture. Serum was evaluated for total calcium and plasma was evaluated for calcitonin. After the final bleeding, the rats were euthanized humanely (by over exposure to $CO_2$).

Measurements: Body weight, serum calcium levels and plasma calcitonin levels.

Data Evaluations: The difference in serum calcium and plasma calcitonin between a treatment group and the vehicle group was determined using a one-way analysis of variance with Dunnett's test, or other multiple comparison methods. Compounds were designated active if $\rho<0.05$ vs. vehicle value.

TABLE IV

Ovarietomy Induced Osteopenia in Rats

| Compound | n | Duration of Assay (weeks) | Percent Protection (trabecular BMD, 30 mg/kg/day, ip) |
|---|---|---|---|
| Example 2 | 8 | 4 | 23 |
| Example 3 | 8 | 4 | 30 |
| Example 4 | 8 | 4 | 35 |
| Example 6 | 8 | 4 | 47* |
| Example 7 | 8 | 4 | 37 |
| Example 8 | 8 | 4 | -2 |
| Example 9 | 8 | 4 | 25 |
| Example 10 | 8 | 4 | -10 |
| Example 12 | 8 | 4 | 50* |
| Example 13 | 8 | 4 | 13 |
| Example 15 | 8 | 4 | 15 |
| Example 18 | 8 | 4 | 52* |

*p < 0.005 vs. vehicle value

These compounds were also tested for their ability to inhibit PDE IV activity since xanthines are known to be potent PDE IV inhibitors Example D Inhibition of Phosphodiesterase IV (PDE-IV) Isolated from Human U937 Cells This assay was used to biochemically assess the ability of a test compound to inhibit PDE-IV isolated from a U937 cell line, where PDE-IV refers to the cGMP-insensitive, cAMP-selective PDE.

Cell Culture: U937 cells were grown in RPMI 1640 medium supplemented with 10% heat-inactivated fetal calf serum and Penicillin/Streptomycin (100 units/100 μg per mL) in a humidified 5% $CO_2$ atmosphere at 37° C. Starter cells were maintained in continuous logarithmic growth by seeding them in 75 $cm^2$ vented tissue culture flasks at a concentration of $3\times10^4$ cells/mL and passing them every 3–4 days when the cells reached approximately $8\times10^5$ cells/mL. For experiments, 3–4 day starter cells were seeded in 225 $cm^2$ flasks at $1\times10^5$ cells/mL and harvested 3–4 days later at approx. $6\times10^5$ cells/mL.

Isolation of PDE-IV: U937 cells were activated with 10 μM dibutyryl cAMP for a period of 4 hours (to up-regulate PDE-IV) and then harvested by centrifugation at 1200×g for 10 min in 250 mL conical centrifuge tubes. The pellet from each 200 mL flask was resuspended in 5 mL buffer A [10 mM Tris-HCl, 5 mM $MgCl_2$, 4 mM EGTA, 5 mM 2-mercaptoethanol, 1 μM leupeptin, 1 μM pepstatin A, and 5 μM phenylmethyl sulfonyl fluoride (PMSF) (pH 7.8)], and the cells were lysed using 3 cycles of freezing (3 min in dry ice/acetone) followed by thawing (warm water). The extract was centrifuged for 20 min. at 1200×g to remove cell debris and the supernatant was immediately loaded onto a 1.6×70 cm DEAE-Sepharose CL-6B anion exchange column equilibrated with buffer A. The column was next washed with 2.5 column volumes of buffer B [10 mM Tris-HCl, 5 mM 2-mercaptoethanol, 0.1 μM leupeptin, 0.1 μM pepstatin A and 0.1 μM PMSF (pH 7.8)], and PDEs were eluted with a step gradient consisting of 80 mL each of buffer B containing 0.4 M or 0.7 M sodium acetate (80 mL/hour, 8 mL/fraction). To determine which families of PDEs were present, fractions may be assayed for hydrolytic activity with 1 μM [$^3$H]- cAMP or 1 μM [$^3$H]-cGMP. Additionally, 1 μM [$^3$H]- cAMP assays were conducted in the presence of 10 μM rolipram, 10 μM cGMP, or calmodulin (1 unit/0.4 mL plus 10 μM $CaCl_2$).

When prepared in this manner, approximately 80% of total cAMP PDE activity is eluted by Buffer B containing 0.7 M sodium acetate. This PDE activity consists of >90% PDE-IV (as evidenced by its susceptibility to inhibition by rolipram.

PDE assay: PDE activity was measured using a modification of the radioisotope procedure previously described by Thompson et al.(Thompson, W. J., Terasaki, W. L., Epstein, P. M. and Strada, S. J. *Adv, Cyclic Nucleotide Res*. 1979, 10, 69). Reaction mixtures (0.4 mL) contain 40 mM Tris-HCl (pH 7.8), 4 mM 2-mercaptoethanol, 5 mM $MgCl_2$, 0.1 μM leupeptin, 0.1 μM pepstatin A, 0.1 μM PMSF, 1 μM [3H]-cAMP or 1 μM [$^3$H]-cGMP (~200,000 DPM), and enzyme to initiate the reaction. $^3$H-cAMP substrate was prepared as follows: A stock solution of $^3$H-cyclic nucleotide (1000 μCi/mL) was diluted 1:10 in 50% EtOH. 200 μl of this diluted stock solution was added to a cold (unlabeled) cyclic nucleotide solution, made at a concentration of 4 μM. 100 μl of this solution was used per assay tube to achieve a final concentration of 1 μM cyclic nucleotide per assay tube (200,000 DPM). Enzyme activity was determined at 37° C. Reactions were terminated by boiling, incubating with snake venom, and cooling as previously described (Thompson et al., 1979). The reaction mixture was applied to a (0.8×8.5 cm) column containing 0.4 g Dowex I-X8 affinity resin; reaction tubes were rinsed with 0.5 mL of methanol; and this, along with an extra 1 mL of methanol, was applied to the column to elute the $^3$H-reaction products. After all liquid has passed through the column, the column was plunged with a 12 cc syringe plunger. Each column's eluate was collected in a 20 mL scintillation vial containing 10 mL aquasol-2 and counted by scintillation spectrophotometry. [$^3$H]-adenosine or [$^3$H]-guanosine recovery was corrected for background DPM determined in the absence of enzyme. The amount of enzyme and duration of assay were adjusted to ensure that less than 25% of the substrate was consumed under these conditions. PDE activities of U937 cell PDE-IV preparations have been found to linear for at least 30 minutes. To test inhibition of PDE-IV, a test compounds was added to the reaction mixture, at concentrations ranging from 0.001 μM to 10 μM.

Measurements: Inhibition by a test compound was measured as a percent reduction of total PDE activity, and calculated as follows:

$$\frac{A}{B} \times 100 = \text{PERCENT INHIBITION OF } PDE\text{-IV}$$

where A is the PDE activity (mean DPM - background DPM) in the presence of test compound, and B is the total PDE-IV activity (mean DPM - background DPM) in the absence of test compound. These percent inhibition of PDE IV values were normalized to rolipram where the rolipram percent inhibition of PDE IV is set to 0%.

$IC_{50}$s are then estimated by linear regression analysis using the percent inhibition data bracketing 50% inhibition.

TABLE V

Phosphodiesterase IV Inhibitory Activity

| Compound | n | % Inhibition of PDE IV (normalized to rolipram) | $IC_{50}$ |
|---|---|---|---|
| Example 1 | 2 | 16 | 25.2 |
| Example 2 | 3 | 97 | — |
| Example 3 | 2 | 87 | — |
| Example 4 | 3 | 41 | 1.2 |
| Example 5 | 1 | 52 | — |
| Example 6 | 2 | 44 | 4.1 |
| Example 7 | 3 | 83 | — |
| Example 8 | 3 | 82 | — |
| Example 9 | 1 | 93 | 3.2 |
| Example 10 | 2 | 89 | — |
| Example 12 | 3 | 42 | 6.0 |
| Example 13 | 3 | 66 | — |
| Example 14 | 1 | 20 | — |
| Example 15 | 1 | 35 | 5.2 |
| Example 16 | 1 | 38 | 6.0 |
| Example 17 | 2 | 24 | — |
| Example 18 | 2 | 37 | 23.3 |
| Example 19 | 1 | 5 | — |
| Example 20 | 1 | 58 | — |

Hence, the compounds of this invention have a pronounced effect on increasing both calcitonin transcription and plasma calcitonin levels and are useful in the treatment of disorder associated with high turnover bone loss, such as Paget's Disease, post menopausal osteoporosis, senile osteoporosis, and glucocorticoid-induced osteoporosis as mentioned above, by administration, orally parenterally, or by aspiration to a patient in need thereof. In addition, these compounds are moderate to weak inhibitors of PDE IV, and biological effects of inhibiting this phosphodiesterase should not be seen on compound administration.

Example 1

1,3-Dibutyl-7-methanesulfonyl-3,7-dihydro-purine-2,6-dione

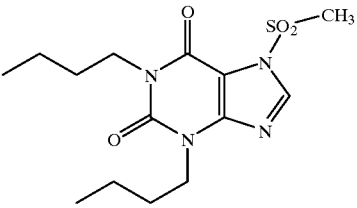

To 500 mg (1.89 mmol) of 1,3-dibutyl-3,7-dihydro-purine-2,6-dione in 30 mL of acetone at 23° C. was added 1.04 g (7.56 mmol) of potassium carbonate followed by 0.15 mL (216 mg, 1.89 mmol) of methanesulfonyl chloride. After stirring at 23° C. for 30 min, the reaction mixture was filtered, the filtrate collected and evaporated to give a white solid. This solid was then triturated with 30 mL of petroleum ether to give 500 mg (1.46 mmol, a 77% yield) of the title compound as a white crystalline solid. mp: 98–100° C.; $^1$H NMR (300 MHz, CDCl$_3$); δ 0.93–0.99 (m, 6H), 1.42–1.49 (m, 4H), 1.55–1.58 (m, 2H), 1.60–1.70 (m, 2H), 3.85 (s, 3H), 3.99–4.04 (m, 2H), ), 4.05–4.16 (t, 2H), 8.17 (s, 1H), 8.55; IR (KBr, cm$^{-1}$): 3144w, 2965m, 2938m, 2876w, 1715s, 1663s, 1537s, 1442m, 1397s, 1182s, 1131,m, 761m, 670m; MS (ES) m/z (relative intensity): 343 (M$^+$+H, 100).

Anal. Calcd. for C$_{14}$H$_{22}$N$_4$O$_4$S; Calculated: C, 49.11; H, 6.48, N, 16.36. Found: C, 49.21; H, 6.56; N, 16.58.

Example 2

7-(Butane-1-sulfonyl)-1,3-dibutyl-3,7-dihydro-purine-2,6-dione

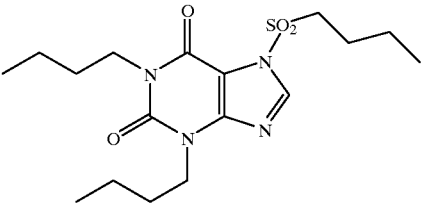

The title compound was prepared according to the procedure of example 1 except that butanesulfonyl chloride was used in place of methanesulfonyl chloride. Yield: 52%; mp: 55–57° C.; $^1$H NMR (300 MHz, CDCl$_3$): δ 0.93–0.99 (m, 9H), 1.39–1.88 (m, 11H), 3.98–4.09 (m, 6H), 4.10–4.19 (m, 4H), 8.14 (s, 1H); IR (KBr, cm$^{-1}$): 3110 w, 2956m, 2931m, 2872w, 1717s, 1672s, 1616m, 1466sm, 1453s, 1440s, 1310w, 1194s, 855m, 741m, 634m, 525m; MS (ES) m/z (relative intensity): 385 (M$^+$+H, 100).

Anal. Calcd. for C$_{17}$H$_{28}$N$_4$O$_4$S; Calculated: C, 53.11; H, 7.34; N, 14.57. Found: C, 52.75; H, 7.49; N, 14.25.

Example 3

1,3-Dibutyl-7-(3-nitro-benzenesulfonyl)-3,7-dihydro-purine-2,6-dione

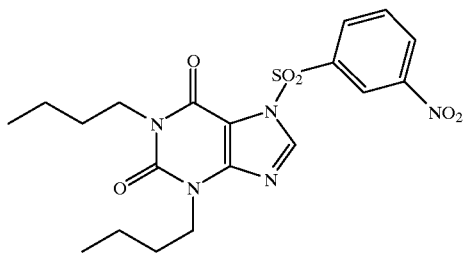

To 404 mg (1.53 mmol) of 1,3-dibutyl-3,7-dihydro-purine-2,6-dione in 15 mL of $CH_2Cl_2$ at 23° C. was added 0.40 mL (296 mg, 2.29 mmol) i-$Pr_2$NEt followed by 373 mg (1.68 mmol) of 3-nitrobenzenesulfonyl chloride. After stirring at 23° C. for 19 h, the reaction mixture was poured into 50 mL brine and extracted with 3×50 mL of EtOAc. The combined organics were successively washed with 1×50 mL sat. $NaHCO_3$ solution, 1×50 mL $H_2O$, 1×50 mL brine, dried over $MgSO_4$, filtered and evaporated to an oily yellow solid. Flash chromatography on silica gel, eluting with $CH_2Cl_2$/EtOAc (40/1), gave a white solid. Recrystallization from hot hexanes/EtOAc gave 540 mg (1.20 mmol, a 79% yield) of the title compound as a white, crystalline solid. mp: 178–179° C.; $^1$H NMR (300 MHz, $CDCl_3$); δ 0.88–0.98 (m, 6H), 1.22–1.42 (m, 4H), 1.50–1.61 (m, 2H), 1.63–1.75 (m, 2H), 3.92 (t, J=7.5 Hz, 2H), 4.07 (t, J=7.5 Hz, 2H) 7.86 (t, J=8.1 Hz, 1H), 8.34 (s, 1H), 8.55 (d, J=8.1 Hz, 1H), 8.77 (d, J=8.2 Hz, 1H), 9.01 (brt, 1H); IR (KBr, $cm^{-1}$): 3142w, 2963m, 2935m, 2876w, 1716s, 1661s, 1538s, 1441m, 1396s, 1181s, 1130m, 761m, 670m; MS (ES) m/z (relative intensity): 450 ($M^+$+H, 100).

Anal. Calcd. for $C_{19}H_{23}N_5O_6S$; Calculated: C, 50.77; H, 5.16, N, 15.58. Found: C, 50.95; H, 5.08; N, 15.71.

Example 4

1,3-Dibutyl-7-(3,4-dimethoxy-benzenesulfonyl)-3,7-dihydro-purine-2,6-dione

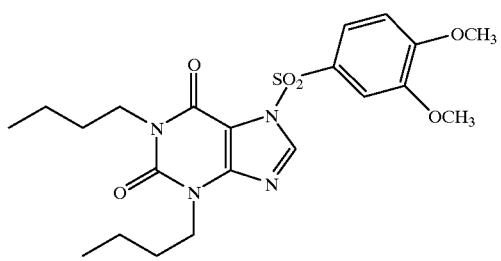

The title compound was prepared according to the procedure of example 3 except that 3,4-dimethoxybenzenesulfonyl chloride was used in place of 3-nitrobenzenesulfonyl chloride. Yield: 81%; mp: 134–135° C.; $^1$H NMR (300 MHz, $CDCl_3$): δ 0.88–0.99 (m, 6H), 1.30–1.43 (m, 4H), 1.50–1.62 (m, 2H), 1.63–1.76 (m, 2H), 3.91–4.00 (m, 2H) 3.95 (s, 3H), 3.99 (s, 3H), 4.09 (t, J=7.5 Hz, 2H), 6.98 (d, J=8.7 Hz, 1H), 7.86 (dd, J=2.3, 8.7 Hz, 1H), 7.97 (d, J=2.3 Hz, 1H), 8.25 (s, 1H); IR (KBr, $cm^{-1}$): 3134w, 2957m, 2933m, 2870w, 1712s, 1668s, 1608m, 1513s, 1438s, 1389s, 1273s, 1170s, 1024m, 760m, 680m, 620m; MS (ES) m/z (relative intensity): 465 ($M^+$+H, 100).

Anal. Calcd. for $C_{21}H_{28}N_4O_6S$; Calculated: C, 54.30; H, 6.08; N, 12.06. Found: C, 54.28; H, 6.17; N, 11.94.

Example 5

1,3-Dibutyl-7-(thiophene-2-sulfonyl)-3,7-dihydro-purine-2,6-dione

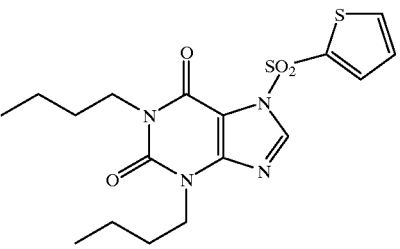

The title compound was prepared according to the procedure of example 3 except that 2-thiophenesulfonyl chloride was used in place of 3-nitrobenzenesulfonyl chloride. Yield: 63%; mp: 145–146° C.; $^1$H NMR (300 MHz, $CDCl_3$): δ 0.90–0.99 (m, 6H), 1.31–1.46 (m, 4H), 1.55–1.76 (m, 4H), 3.98 (t, J=7.4 Hz, 2H), 4.08 (t, J=7.4 Hz, 2H), 7.19 (t, J=4.0 Hz, 1H), 7.83 (dd, J=1.4, 5.0 Hz, 1H), 8.26 (s, 1H), 8.33 (dd, J=1.4, 4.0 Hz, 1H); IR (KBr, $cm^{-1}$): 3094w, 3080w, 2960w, 2933w, 1713s, 1670s, 1613w, 1524w, 1392s, 1176s, 1124w, 685m, 591m.; MS (ES) m/z (relative intensity): 411 ($M^+$+H, 100).

Anal. Calcd. for $C_{17}H_{22}N_4O_4S_2$; Calculated: C, 49.74; H, 5.40; N, 13.65. Found: C, 49.58; H, 5.32; N, 13.65.

Example 6

1,3-Dibutyl-7-(3-chloro-propane-1-sulfonyl)-3,7-dihydro-purine-2,6-dione

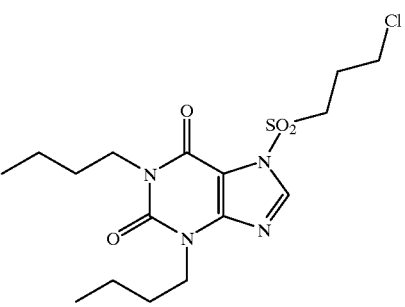

The title compound was prepared according to the procedure of example 3 except that 3-chloropropanesulfonyl chloride was used in place of 3-nitrobenzenesulfonyl chloride. Yield: 90%; mp: 71–73° C.; $^1$H NMR (300 MHz, $CDCl_3$): δ 0.91–1.01 (m, 6H), 1.31–1.49 (m, 4H), 1.57–1.68 (m, 2H), 1.69–1.81 (m, 2H), 2.31–2.41 (m, 2H), 3.69 (t, J=6.1 Hz, 2H), 4.01 (t, J=7.5 Hz, 2H), 4.12 (t, J=7.5 Hz, 2H), 4.23 (t, J=7.5 Hz, 2H), 8.15 (s, 1H); IR (KBr, cm-1); IR (KBr, $cm^{-1}$): 3112s, 2958s, 2934s, 2873m, 1704s, 1670s, 1528m, 1441s, 1358m, 1165m, 1125m, 763m, 751m, 529m; MS (ES) m/z (relative intensity): 405 ($M^+$+H).

Anal. Calcd. for $C_{16}H_{25}ClN_4O_4S$; Calculated: C, 47.46; H, 6.22; N, 13.84. Found: C, 47.31; H, 6.3 1; N, 13.5 8.

Example 7

1,3-Dibutyl-7-(naphthalene-1-sulfonyl)-3,7-dihydro-purine-2,6-dione

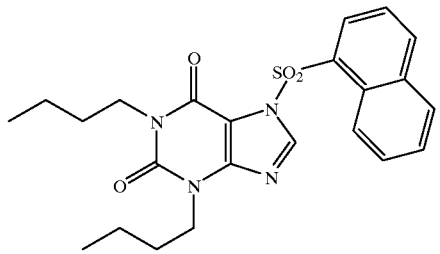

The title compound was prepared according to the procedure of example 3 except that 1-naphthylsulfonyl chloride was used in place of 3-nitrobenzenesulfonyl chloride. Yield: 80%; mp: 135–136° C.; $^1$H NMR (300 MHz, CDCl$_3$): δ 0.82–0.97 (m, 6H), 1.20–1.39 (m, 4H), 1.41–1.53 (m, 2H), 1.60–1.72 (m, 2H), 3.83 (t, J=7.5 Hz, 2H) 4.02 (t, J=7.5 Hz, 2H), 7.57–7.78 (m, 3H), 7.98 (d, J=8.2 Hz, 1H), 8.22 (d, J=8.1 Hz, 1H), 8.47 (d, J=8.2 Hz, 1H), 8.55 (s, 1H), 8.97 (d, J=8.2 Hz, 1H); IR (KBr, cm$^{-1}$): 3141w, 2959w, 2933w, 2972w, 1712s, 1664s, 1612w, 1381m, 1171m, 764m, 608w; MS (ES) m/z (relative intensity): 455 (M$^+$+H, 100).

Anal. Calcd. for C$_{23}$H$_{26}$N$_4$O$_4$S; Calculated: C, 60.78; H, 5.77; N, 12.33. Found: C, 60.62; H, 5.57; N, 12.11.

Example 8

1,3-Dibutyl-7-(4-hydroxyamino-benzenesulfonyl)-3,7-dihydro-purine-2,6-dione

Step 1

1,3-Dibutyl-7-(4-nitro-benzenesulfonyl)-3,7-dihydro-purine-2,4-dione

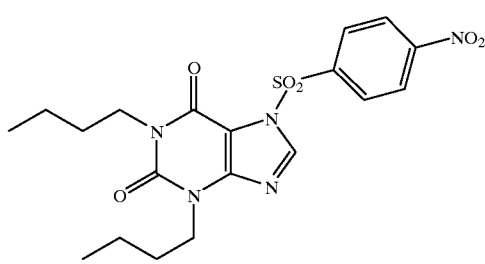

The title compound was prepared according to the procedure of example 3 except that 4-nitrobenzenesulfonyl chloride was used in place of 3-nitrobenzenesulfonyl chloride. Yield: 77%: mp: 138–139° C.; $^1$H NMR (300 MHz, CDCl$_3$): δ 0.89–0.98 (m, 6H), 1.29–1.42 (m, 3H), 1.52–1.62 (m, 3H), 1.65–1.74 (m, 2H), 3.92 (t, J=7.5 Hz, 2H), 4.08 (t, J=7.5 Hz, 2H), 8.31 (s, 1H), 8.42 (d, J=8.1 Hz, 2H), 8.51 (d, J=8.1 Hz, 2H); IR (KBr, cm-1); IR (KBr, cm$^{-1}$): 3109w, 2956m, 2931m, 2872w, 1716s, 1671s, 1615m, 1537s, 1523s, 1440m, 1178s, 1124s, 855m, 741m, 634m; MS (ES) m/z (relative intensity): 450 (M$^+$+H, 100).

Anal. Calcd. for C$_{19}$H$_{23}$N$_5$O$_6$S; Calculated: C, 50.77; H, 5.16; N, 15.58. Found: C, 50.60; H, 4.96; N, 15.51.

Step 2

1,3-Dibutyl-7-(4-hydroxyamino-benzenesulfonyl)-3,7-dihydro-purine-2,6-dione

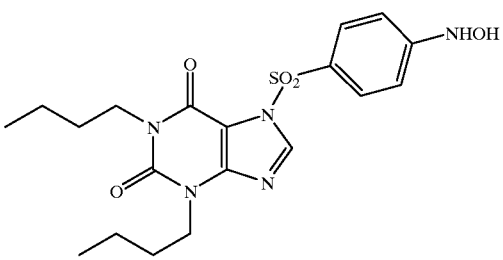

1,3-Dibutyl-7-(4-nitro-benzenesulfonyl)-3,7-dihydro-purine-2,4-dione (4.26 g, 10.57 mmol), 1.0 g of 10% Pd/C and 100 mL of EtOAc were placed under 1 atmosphere of H$_2$ and stirred at 23° C. for 8 h. The reaction mixture was filtered through Celite and evaporated to give an off-white solid. Recrystallization from hot hexanes/EtOAc gave 3.91 g (8.98 mmol, an 85% yield) of the title compound as a white, crystalline solid. mp: 148–150° C.; $^1$H NMR (300 MHz, CDCl$_3$): δ 0.88–0.98 (m, 6H), 1.35 (sept, J=8.0 Hz, 4H), 1.51–1.61 (m, 2H), 1.61–1.73 (m, 2H), 3.93 (t, J=7.5 Hz, 2H), 4.08 (t, J=7.5 Hz, 2H), 5.85 (s, 1H), 7.03 (d, J=8.1 Hz, 2H), 7.19 (brs, 1H), 8.11 (d, J=8.1 Hz, 2H), 8.26 (s, 1H); IR (KBr, cm$_{-1}$): 3400–2830 brm, 3255m, 2957m, 2872w, 1707s, 1659s, 1595s, 1524m, 1433m, 1384m, 1167s, 1120m, 588m; MS (ES) m/z (relative intensity): 436 (M$^+$+H, 100).

Anal. Calcd. for C$_{19}$H$_{25}$N$_5$O$_6$S; Calculated: C, 52.40; H, 5.79; N, 16.08. Found: C, 52.68; H, 5.76; N, 16.10.

Example 9

1,3-Dibutyl-7-phenylmethanesulfonyl-3,7-dihydro-purine-2,6-dione

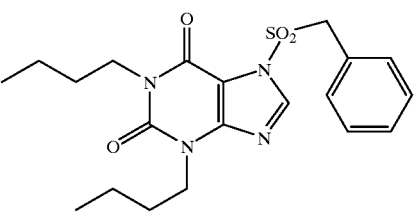

The title compound was prepared according to the procedure of example 3 except that benzylsulfonyl chloride was used in place of 3-nitrobenzenesulfonyl chloride. Yield: 56%; mp: 117–118° C.; $^1$H NMR (300 MHz, CDCl$_3$): δ 0.90–1.01 (m, 6H), 1.31–1.52 (m, 4H), 1.62–1.79 (m, 4H), 4.00–4.13 (m, 4H), 5.23 (s, 2H), 7.21–7.43 (m, 5H), 7.77 (s, 1H); IR (KBr, cm$^{-1}$): 3140w, 2981w, 2959w, 2933w, 1705s, 1672s, 1520w, 1438s, 1184m, 782w, 761m; MS (ES) m/z (relative intensity): 419 (M$^+$+H, 100).

Anal. Calcd. for C$_{20}$H$_{26}$N$_4$O$_4$S; Calculated: C, 57.40; H, 6.26; N, 13.39. Found: C, 57.45; H, 6.23; N, 13.28.

Example 10

1,3-Dibutyl-7-(7,7-dimethyl-2-oxo-bicyclo[2.2.1]hept-1-ylmethanesulfonyl)-3,7-dihydro-purine-2,6-dione

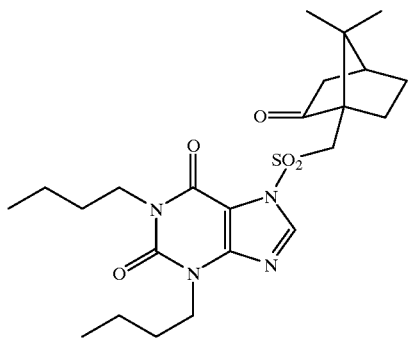

The title compound was prepared according to the procedure of example 3 except that (1R)-(-)-10-camphorsulfonyl chloride was used in place of 3-nitrobenzenesulfonyl chloride. Yield: 45%; mp: 55–56° C.; $[\alpha]_D = -25°$ (c. 0.005, CHCl$_3$); $^1$H NMR (300 MHz, CDCl$_3$): δ 0.85–1.05 (m, 6H), 0.97 (s, 3H), 1.16 (s, 3H), 1.27–1.29 (m, 1H), 1.33–1.42 (m, 4H), 1.47–1.53 (m, 1H), 1.53–1.65 (m, 2H), 1.65–1.,83 (m, 2H), 1.93 (d, J=14.9 Hz, 1H), 2.04–2.19 (m, 2H), 2.37–2.49 (m, 2H), 4.02 (t, J=7.5 Hz, 2H), 4.08 (s, 1H), 4.08 (t, J=7.5 Hz, 2H), 4.33 (d, J=14.9 Hz, 1H), 8.14 (s, 1H); IR (KBr, cm$^{-1}$): 3153w, 2955m, 2934m, 2906m, 1749m, 1711s, 1665s, 1608m, 1375m, 1166m, 764w; MS (ES) m/z (relative intensity): 479 (M$^+$+H, 100).

Anal. Calcd. for C$_{23}$H$_{34}$N$_4$O$_5$S; Calculated: C, 57.72; H, 7.16; N, 11.71. Found: C, 58.02; H, 7.46; N, 11.38.

Example 11

N-Acetoxy-N-[4-(1,3-dibutyl-2,6-dioxo-1,2,3,6-tetrahydro-purine-7-sulfonyl)-phenyl]-acetamide

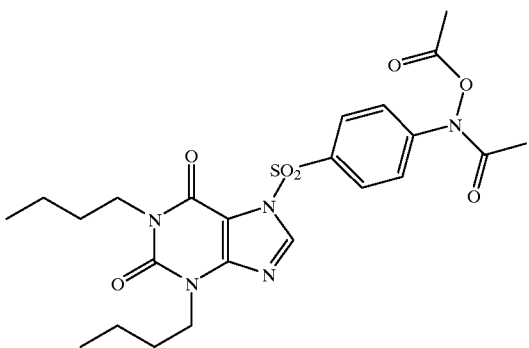

To a 23° C. solution of 300 mg (0.69 mmol) of 1,3-dibutyl-7-(4-hydroxyamino-benzenesulfonyl)-3,7-dihydro-purine-2,6-dione and 7 mL of pyridine was added 0.12 mL (119 mg, 1.52 mmol) of acetyl chloride. After stirring 15 h, 50 mL of toluene was added the reaction mixture was evaporated. The residue was dissolved in 25 mL EtOAc/25 mL brine, extracted and the organic layer was washed with 2×25 mL H$_2$O, 1×25 mL brine, dried over MgSO$_4$, filtered and evaporated to a light yellow oil. Flash chromatography on silica gel, eluting with CH$_2$Cl$_2$/EtOAc (20/1 to 8/1) gave an off-white solid. Recrystallization from hot hexanes/EtOAc gave 262 mg (0.50 mmol, a 73% yield) of the title compound as a white, crystalline solid. mp: 155–157° C.; $^1$H NMR (300 MHz, CDCl$_3$): δ 0.90–0.99 (m, 6H), 1.38 (sept, J=7.5 Hz, 4H), 1.51–1.62 (m, 2H), 1.62–1.75 (m, 2H), 2.21 (s, 3H), 2.34 (s, 3H), 3.94 (t, J=7.5 Hz, 2H) 4.07 (t, J=7.5 Hz, 2H), 7.70 (d, J=8.1 Hz, 2H), 8.26 (s, 1H), 8.27 (d, J=8.1 Hz, 2H); IR (KBr, cm$^{-1}$): 2959w, 2934w, 2873w, 1806w, 1711s, 1669s, 1608w, 1370w, 1290m, 1174m, 695m; MS (ES) m/z(relative intensity): 520 (M++H, 100).

Anal. Calcd. for C$_{23}$H$_{29}$N$_5$O$_7$S; Calculated: C, 53.17; H, 5.63; N, 13.48. Found: C, 53.01; H, 5.65; N, 13.23.

Example 12

1,3-Dibutyl-7-(2,4,6-trimethyl-benzenesulfonyl)-3,7-dihydro-purine-2,6-dione

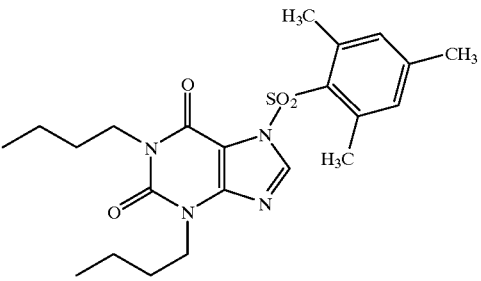

The title compound was prepared according to the procedure of example 3 except that 2,4,6-trimethylbenzenesulfonyl chloride was used in place of 3-nitrobenzenesulfonyl chloride. Yield: 90%; mp: 125–127° C.; $^1$H NMR (300 MHz, CDCl$_3$): δ 0.87 (t, J=7.2 Hz, 3H), 0.96 (t, J=7.2 Hz, 3H), 1.15–1.30 (m, 2H), 1.30–1.48 (m, 2H), 1.49–1.56 (m, 2H), 1.65–1.78 (m, 2H), 2.32 (s, 3H), 2.61 (s, 6H), 3.83 (t, J=7.4 Hz, 2H), 4.14 (t, J=7.4 Hz, 2H), 7.00 (s, 2H), 8.35 (d, J=2.1 Hz, 1H); IR (KBr, cm$^{-1}$): 3138w, 2956w, 2931s, 2869w, 1712s, 1673s, 1363s, 1197m, 1177m, 1120m, 663s; MS (ES) m/z (relative intensity): 447 (M$^+$+H, 100). Anal. Calcd. for C$_{22}$H$_{30}$N$_4$O$_4$S; Calculated: C, 59.17; H, 6.77; N, 12.55. Found: C, 59.30; H, 6.80; N, 12.55.

Example 13

1,3-Dibutyl-7-(4-tert-butyl-benzenesulfonyl)-3,7-dihydro-purine-2,6-dione

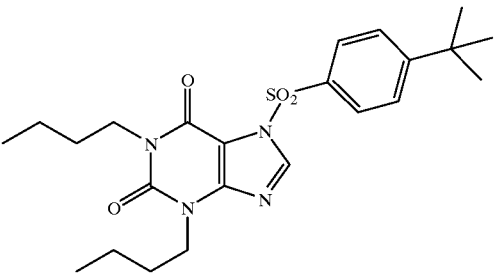

The title compound was prepared according to the procedure of example 1 except that 4-tert-butylbenzenesulfonyl chloride was used in place of methanesulfonyl chloride. Yield: 57%; mp: 105–107° C.; $^1$H NMR (300 MHz, CDCl$_3$):

δ 0.90–0.97 (m, 6H), 1.36 (s, 9H), 1.35–1.42 (m, 4H), 1.64–1.74 (m, 4H), 3.73 (t, J=7.2 Hz, 2H), 4.06 (t, J=7.5 Hz, 2H), 7.60 (d, J=8.7 Hz, 2H), 8.18 (d, J=8.8 Hz, 2H), 8.28 (s, 1H); IR (KBr, cm$^{-1}$): 3130w, 2958m, 2869m, 1714s, 1671s, 1608m, 1591m, 1524s, 1464m, 1183s, 1121s, 838m, 758m, 636m; MS (ES) m/z (relative intensity): 461 (M$^+$+H, 100).

Anal. Calcd. for $C_{23}H_{32}N_4O_4S$; Calculated: C, 59.98; H, 7.00; N, 12.16. Found: C, 60.00; H, 7.00; N, 12.15.

Example 14

1,3-Dibutyl-7-(3,5-dimethyl-isoxazole-4-sulfonyl)-3,7-dihydro-purine-2,6-dione

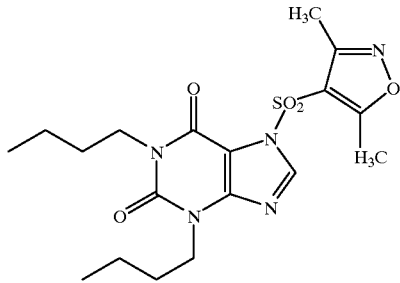

The title compound was prepared according to the procedure of example 1 except that 3,5-dimethylisoxazole-4-sulfonyl chloride was used in place of methanesulfonyl chloride. Yield: 96%; mp: 103–105° C.; $^1$H NMR (300 MHz, CDCl$_3$): δ 0.91–0.99 (m, 6H), 1.29–1.43 (m, 4H), 1.51–1.61 (m, 2H), 1.67–1.77 (m, 2H), 2.29 (s, 3H), 2.92 (s, 3H), 3.90 (t, J=7.6 Hz, 2H), 4.09 (t, J=7.5 Hz, 2H), 8.29 (s, 1H); IR (KBr, cm$^{-1}$): 3141w, 2957m, 2869m, 1785s, 1671s, 1610m, 1522s, 1485m, 1183s, 1121s, 938m, 751m, 642m; MS (ES) m/z (relative intensity): 424 (M$^+$+H, 100).

Anal. Calcd. for $C_{18}H_{25}N_5O_5S$; Calculated: C, 51.05; H, 5.95; N, 16.54. Found: C, 51.01; H, 5.97; N, 16.50.

Example 15

3-Butyl-1-(3-methyl-but-2-enyl)-7-(toluene-4-sulfonyl)-3,7-dihydro-purine-2,6-dione

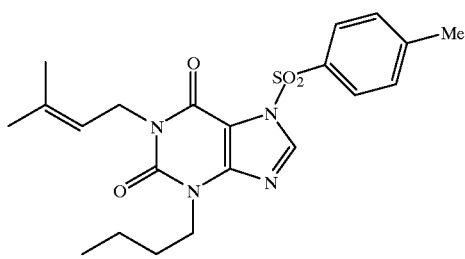

Step 1

1H-3-butyl-7-(toluene-4-sulfonyl)-3,7-dihydropurine-2,6-dione

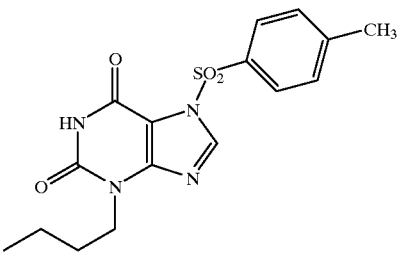

To a suspension of 3.8 g (18.25 mmol) of 3-n-butyl xanthine in 50 mL CH$_2$Cl$_2$ was added 5.0 mL (4.89 g, 0.06 mol) of pyridine, 4.56 g (0.024 mol) of p-toluenesulfonyl chloride, and 1.2 g (0.01 mol) of DMAP. The suspension was stirred at 23° C. for 2 days. Methylene chloride (100 mL) and 50 mL H$_2$O were added, and the undissolved precipitate was filtered and discarded. The organic layer is separated and washed with brine, dried over MgSO4, filtered and evaporated to a white solid. Recrystallization from EtOAc gave 1.0 g (2.75 mmol, a 15% yield) of the title compound as a white solid. mp: 210–212° C.; $^1$H NMR (300 MHz, DMSO-d$_6$) δ 0.87 (t, J=7.5 Hz, 3H), 1.21–1.33(m, 2H), 1.53–1.63 (m, 2H), 2.41 (s, 3H , 3.87 (t, J=7.5 Hz, 2H), 7.50 (d, J=9 Hz, 2H=), 8.09 (d, J=8.5 Hz, 2H), 8.74 (s, 1H), 11.50 (s, 1H); IR (KBr, cm$^{-1}$): 3052w, 1710s, 1690s, 1596m, 1525m, 1370m, 1151s, 669s; MS (ES) m/z (relative intensity ): 363 (M$^+$+H, 100).

Anal. Calcd. for $C_{16}H_{18}N_4O_4S$: Calculated: C, 53.03; H, 5.01; N, 15.46. Found: C, 52.86; H, 4.99; N, 15.59.

Step 2

3-Butyl-1-(3-methyl-but-2-enyl)-7-(toluene-4-sulfonyl)-3,7-dihydro-purine-2,6-dione

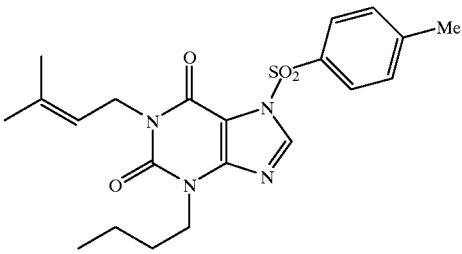

To a suspension of 365 mg (1.00 mmol ) of 1H-3-n-butyl-7-(toluene-4-sulfonyl)-3,7-dihydropurine-2,4-dione in 3 mL DMF was added 165 mg (1.2 mmol) of K$_2$CO$_3$, followed by 330 mg (2.2 mmol) of 4-bromo-2-methyl-2-butene. After stirring at 23° C. for 19 h, the reaction mixture was poured into 100 mL of H$_2$O, extracted with 100 mL EtOAc, and the organics were washed with 100 mL brine, dried over MgSO$_4$, filtered and evaporated to a while solid. Trituration with Et$_2$O and filtration gave 240 mg (0.557 mmol, a 56 % yield) of the title compound as a while solid. mp: 130–135° C.; $^1$H NMR (300 MHz, DMSO-d$_6$) δ 0.88 (t, J=7.5 Hz, 3H), 1.22–1.32 (m, 2H), 1.54–1.59 (m, 4H), 1.62 (s, 3H), 1.71 (s, 3H), 2.41 (s, 3H), 3.94 (t, J=7.5 Hz, 2H), 4.35 (d, J=9 Hz, 2H), 5.07 (t, J=12 Hz, 1H), 7.51 (d, J=8.3 Hz , 2H), 8.10 (d, J=8.3 Hz, 2H), 8.78 (s, 1H); IR (KBr, cm$^{-1}$): 3137w, 2956w, 2930w, 1714s, 1660s, 1524m, 1437m, 1392m, 1172s, 1131m, 677m; MS (ES) m/z (relative intensity): 431(M$^+$+H, 100).

Anal. Calcd. for $C_{21}H_{26}N_4O_4S$: Calculated: C, 58.59; H, 6.09; N, 13.01. Found: C, 58.37; H, 5.93; N, 13.01.

Example 16

3-Butyl-1-ethyl-7-(toluene-4-sulfonyl)-3,7-dihydro-purine-2,6-dione

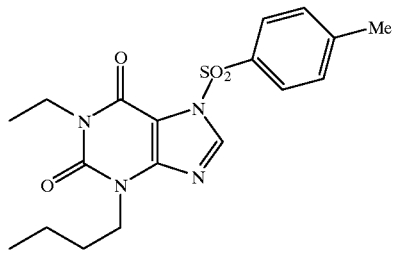

The title compound was prepared according to the procedure of example 15, step 2 except that iodoethane was used in place of 4-bromo-2-methyl-2-butene. mp: 135–139° C.; 1H NMR (300 MHz, DMSO-d$_6$) δ 0.88 (t, J=7.5 Hz, 3H), 1.05 (t, J=7.4, 3H), 1.22–1.34 (m, 4H), 1.55–1.65 (m, 2H), 2.41 (s, 3H), 3.79–3.86 (q, 2H), 3.95 (t, J=6 Hz, 2H), 7.51 (d, J=9 Hz , 2H), 8.12 (d, J=9 Hz, 2H), 8.78 (s, 1H); IR (KBr, cm$^{-1}$): 3137w, 2962w, 2931w, 1717s, 1660s, 1615m, 1433m, 1392m, 1170s, 1124m, 676m; MS (ES) m/z (relative intensity): 391(M$^+$+H, 100).

Anal. Calcd. for $C_{18}H_{22}N_4O_4S$: Calculated: C, 55.37; H, 5.68; N, 14.35. Found: C, 55.28; H, 5.67; N, 14.20.

Example 17

3-Butyl-7-(3,4-dimethoxy-benzenesulfonyl)-1-(3-methyl-but-2-enyl)-3,7-dihydro-purine-2,6-dione

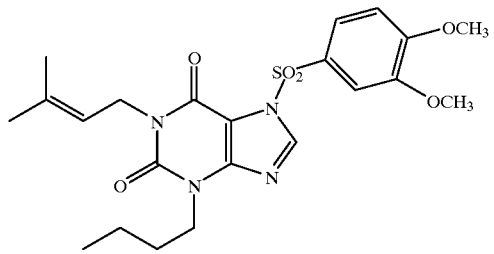

Step 1

3-Buty-7-(3,4-dimethoxy-benzenesulfonyl)-1-H-3,7-dihydro-purine-2,6-dione

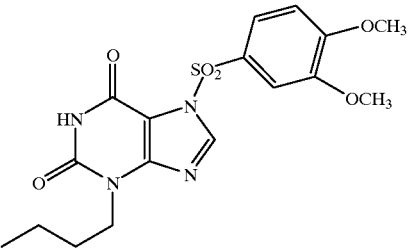

The title compound was synthesized according to the procedure of example 15, step 1, except that 3,4-dimethoxybenzenesulfonyl chloride is used in place of p-toluenesulfonyl chloride. mp: 195–198° C.; $^1$H NMR (300 MHz, DMSO-d$_6$) 0.90 (t, J=7.5 Hz, 3H), 1.23–1.33 (m, 2H), 1.53–1.63(m, 4H), 3.85 (s, 3H), 3.87 (s, 3H), 7.24 (d, J=8.6 Hz , 1H), 7.81 (d, J=2.2 Hz, 1H), 7.84 (dd, J=2.2, 8.6 Hz, 1H), 8.70 (s, 1H) 11.38 (s, 1H); IR (KBr, cm$^{-1}$): 3183w, 1710s, 1597s, 1526m, 1512m, 1142m, 1031s, 677m; MS (ES) m/z (relative intensity): 409(M$^+$+H, 100).

Anal. Calcd. for $C_{17}H_{20}N_4O_6S$; Calculated: C, 49.99; H, 4.94; N, 13.72. Found: C, 49.46; H, 4.93; N, 12.85.

Step 2

3-Butyl-7-(3,4-dimethoxy-benzenesulfonyl)-1-(3-methyl-but-2-enyl)-3,7-dihydro-purine-2,6-dione

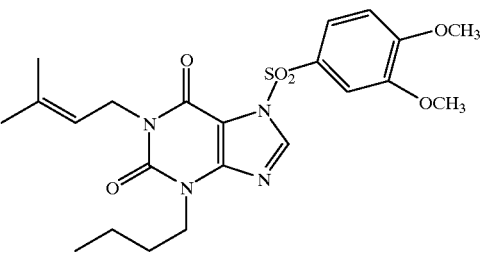

The title compound was synthesized according to the procedure of example 15, step 2, except that of 1H-3-n-butyl-7-(3,4-dimethoxy-benzenesulfonyl)-3,7 dihydropurine-2,4-dione was used in place of 1H-3-n-butyl-7-(toluene-4-sulfonyl)-3,7-dihydropurine-2,4-dione. mp: 92–95° C.; $^1$H NMR (300 MHz, CDCl$_3$) δ 0.94 (t, J=7.5 Hz, 3H ), 1.25–1.41 (m, 2H), 1.54–1.59 (m, 4H), 1.68 (s, 3H), 1.71 (s, 3H), 3.95(s, 3H), 3.98 (s, 3H), 4.06 (t, J=9 Hz, 2H), 4.57 (d, J=6 Hz, 1H), 5.20 (t, J=12 Hz, 1H), 6.95 (d, J=9 Hz , 1H), 7.82 (dd, J=2.1, 10.8 Hz, 1H), 8.05 (d, J=2.1 Hz, 1H) 8.24 (s, 1H); IR (KBr, cm$^{-1}$): 3137w, 2960w, 2934w, 1711s, 1670s, 1606m, 1585m, 1512m, 1271m, 1173m, 671m; MS (ES) m/z (relative intensity ): 477(M$^+$+H, 100).

Anal. Calcd. for $C_{22}H_{28}N_4O_6S$; Calculated: C, 55.45; H, 5.92; N, 11.76. Found: C, 55.14; H, 5.98; N, 11.57.

Example 18

1,3-Dibutyl-7-(4-chloro-2,5-dimethyl-benzenesulfonyl)-3,7-dihydro-purine-2,6-dione

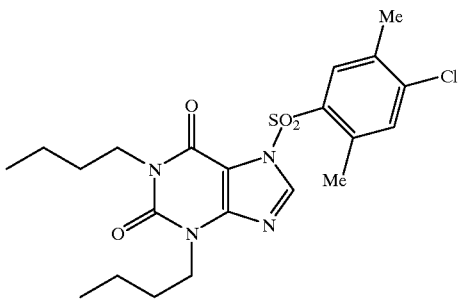

The title compound was prepared according to the procedure of example 3 except that 4-chloro-2,5-dimethylsulfonyl chloride was used in place of methanesulfonyl chloride. Yield: 79%; mp: 138–140° C.; $^1$H NMR (300 MHz, CDCl$_3$): δ 0.88–0.98 (m, 6H), 1.25–1.42 (m, 2H), 1.50–1.59 (m, 2H), 1.67–1.77 (m, 2H), 2.44 (s, 3H), 2.44 (s, 3H), 2.46 (s, 3H), 3.88 (t, J=7.5 Hz, 2H), 4.07 (t, J=7.47 Hz, 2H), 8.33 (s, 1H), 8.46 (s, 1H); IR (KBr, cm$^{-1}$): 3141w, 2957m, 2869m, 1785s, 1671s, 1610m, 1522s, 1485m, 1183s, 1121s, 938m, 751m, 642m; MS (ES) m/z (relative intensity): 467 (M$^+$+H, 100).

Anal. Calcd. for C$_{21}$H$_{27}$ClN$_4$O$_4$S; Calculated: C, 54.01; H, 5.83; N, 12.00. Found: C, 54.05; H, 5.58; N, 12.05.

Example 19

1,3-Dibutyl-7-(3-chloro-propane-1-sulfonyl)-8-methyl-3,7-dihydro-purine-2,6-dione

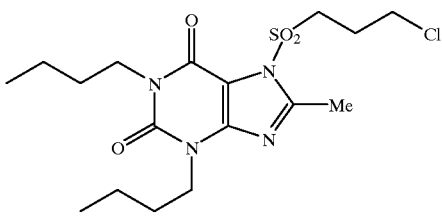

Step 1

1,3-Dibutyl-8-methyl-3,7-dihydro-purine-2,6-dione

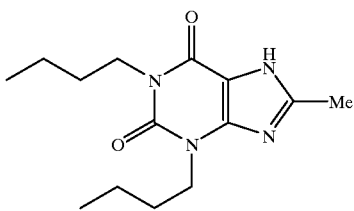

15.0 g (52.8 mmol) 6-amino-1,3-di-n-butyl-5-nitrosouracil, 1.5 g 10% Pd/C and 150 mL DMF were hydrogenated at 40 psi in a Parr shaker for 4 h. After completion, the reaction mixture was filtered through Celite, and evaporated to give crude 5,6-diaminouracil as a dark oil. To this oil was added 20 mL of acetic acid, 40 mL of DMF followed, 16.1 g (84 mmol) of 1 -[3-(dimethylamino)propyl]-3-ethylcarbodiimidehydrochloride, 177 mg (1.45 mmol) of DMAP, and the resulting mixture was stirred overnight. The reaction mixture was concentrated on the rotary evaporator, 100 mL of 2N NaOH was added and this mixture was refluxed for 4 h. After cooling to 23° C., the reaction mixture was adjusted to pH~7 with 6N HCl which caused a precipitate to form. The solid was collected to give 14.1 g (50.69 mmol, a 96% yield) of the title compounds as a yellow solid. mp: 144–146° C.; $^1$H NMR (300 MHz, CDCl$_3$): δ 0.91–0.98 (m, 6H), 1.36–1.46 (m, 4H), 1.64–1.70 (m, 2H), 1.71–1.80 (m, 2H), 2.58 (s, 3H), 4.06–4.14 (m, 4H), 13.10 (brs, 1H); IR (KBr, cm$^{-1}$): 3378w, 3334m, 3047m, 2958m, 2873m, 1701s, 1650s, 1605m, 1562m, 1508m, 1440m, 1177m, 1114m, 920m, 751m, 570m; MS (ES) m/z (relative intensity): 279 (M$^+$+H, 100).

Step 2

1,3-Dibutyl-7-(3-chloro-propane-1-sulfonyl)-8-methyl-3,7-dihydro-purine-2,6-dione

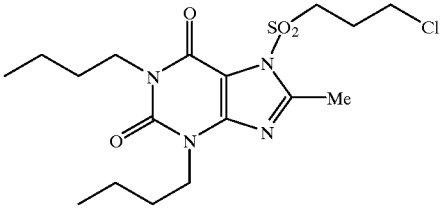

The title compound was prepared according to the procedure of example 3 except that 1,3-dibutyl-8-methyl-3,7-dihydro-purine-2,6-dione was used in place of 1,3-dibutyl-3,7-dihydro-purine-2,6-dione and 3-chloropropanesulfonyl chloride was used in place of methanesulfonyl chloride. Yield: 71%: mp: 76–78° C.; $^1$H NMR (300 MHz, CDCl$_3$): δ 0.92–0.99 (m, 6H), 1.33–1.42 (m, 4H), 1.57–1.65 (m, 2H), 1.67–1.74 (m, 2H), 2.32–2.41 (m, 2H) 2.74 (s, 3H), 3.69 (t, J=6.2 Hz, 2H), 3.99 (t, J=7.6 Hz, 2H), 4.08 (t, J=7.5 Hz, 2H), 4.23 (t, J=7.5 Hz, 2H); IR (KBr, cm$^{-1}$): 2959m, 2874m, 1705s, 1620w, 1537s, 1522s, 1485m, 1183s, 1121s, 938m, 751m, 570m; MS (ES) m/z (relative intensity): 419 (M$^+$+H, 100).

Anal. Calcd. for C$_{17}$H$_{27}$ClN$_4$O$_4$S; Calculated: C, 48.74; H, 6.5; N, 13.37. Found: C, 48.69; H, 6.55; N, 13.03.

Example 20

1,3-Dibutyl-8-methyl-7-(toluene-4-sulfonyl)-3,7-dihydro-purine-2,6-dione

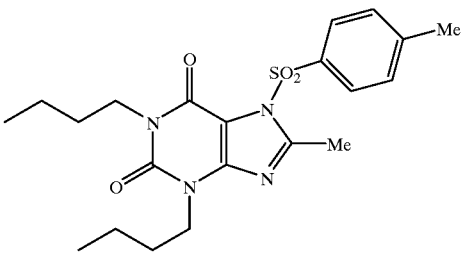

The title compound was prepared according to the procedure of example 3 except that 1,3-dibutyl-8-methyl-3,7- dihydro-purine-2,6-dione was used in place of 1,3-dibutyl-3,7-dihydro-purine-2,6-dione and p-toluenesulfonyl chloride was used in place of methanesulfonyl chloride. Yield: 75%; mp: 111–113° C.; $^1$H NMR (300 MHz, CDCl$_3$): δ 0.89–0.96 (m, 6H), 1.29–1.37 (m, 4H), 1.58–1.65 (m, 2H), 1.67–1.72 (m, 2H), 2.48 (s, 3H), 2.86 (s, 3H), 3.93 (t, J=7.6 Hz, 2H), 4.11 (t, J=7.1 Hz, 2H), 7.36 (d, J=8.1 Hz, 2H), 8.13 (d, J=8.5 Hz, 2H); IR (KBr, cm$^{-1}$): 2960m, 2865m, 1709s, 1674s, 1593m, 1528s, 1479m, 1181m, 1121s, 938m, 760m, 595m; MS (ES) m/z (relative intensity): 433 (M$^+$+H, 100).

Anal. Calcd. for $C_{21}H_{28}N_4O_4S$; Calculated: C, 58.31; H, 6.52; N, 12.95. Found: C, 58.19; H, 6.59; N, 12.83.

We claim:

1. A compound of formula (I)

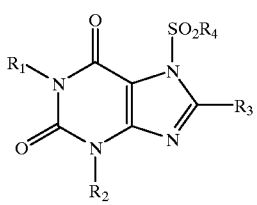

(I)

wherein:

$R_1$ and $R_2$ are independently alkyl of 1 to 6 carbon atoms, allyl, or substituted allyl of 3 to 6 carbon atoms;

$R_3$ is hydrogen, alkyl of 1 to 6 carbon atoms, or cycloalkyl of 3 to 10 carbon atoms;

$R_4$ is phenyl or naphthyl substituted with alkyl of 1 to 6 carbon atoms, alkoxy of 1 to 6 carbon atoms or $NR_5R_6$; substituted or unsubstituted phenylalkyl wherein the alkyl group contains 1 to 6 carbon atoms; substituted or unsubstituted 5 to 10 membered heteroaryl having 1 to 3 heteroatoms selected from N, S and O; substituted or unsubstituted cycloalkyl of 3 to 10 carbon atoms; or substituted or unsubstituted cycloalkylalkyl of 4 to 10 carbon atoms; provided that phenyl or naphthyl is substituted with $NR_5R_6$ when $R_1$ and R2 is alkyl;

$R_5$ and $R_6$ are independently selected from H, —OH, —COR$_7$, —OCOR$_7$; provided that $R_5$ and $R_6$ are not both H; and $R_7$ is alkyl of 1 to 6 carbon atoms; or a pharmaceutical salt thereof.

2. A compound according to claim 1 wherein:

$R_1$ and $R_2$ are independently alkyl of 1 to 6 carbon atoms;

$R_3$ is H; and $R_4$ is phenyl or naphthyl, substituted with $NR_5R_6$; or substituted or unsubstituted 4 to 6 membered heteroaryl.

3. A compound according to claim 1 wherein $R_1$ is allyl.

4. A compound according to claim 1 wherein $R_4$ is cycloalkylalkyl of 6 to 10 carbon atoms phenylalkyl wherein the alkyl group has 1 to 6 carbon atoms.

5. A compound of claim 1 which is 1,3-dibutyl-7-(thiophene-2-sulfonyl)-3,7-dihydro-purine-2,6-dione or a pharmaceutically acceptable salt thereof.

6. A compound of claim 1 which is 1,3-dibutyl-7-(4-hydroxyamino-benzenesulfonyl)-3,7-dihydro-purine-2,6-dione or a pharmaceutically acceptable salt thereof.

7. A compound of claim 1 which is 1,3-dibutyl-7-phenylmethanesulfonyl-3,7-dihydro-purine-2,6-dione or a pharmaceutically acceptable salt thereof.

8. A compound of claim 1 which is 1,3-dibutyl-7-(7,7-dimethyl-2-oxo-bicyclo[2.2.1 ]hept-1 -ylmethanesulfonyl)-3,7-dihydro-purine-2,6-dione or a pharmaceutically acceptable salt thereof.

9. A compound of claim 1 which is N-acetoxy-N-[4-(1,3-dibutyl-2,6-dioxo-1,2,3,6-tetrahydro-purine-7-sulfonyl)-phenyl]-acetamide or a pharmaceutically acceptable salt thereof.

10. A compound of claim 1 which is 1,3-dibutyl-7-(3,5-dimethyl-isoxazole-4-sulfonyl)-3,7-dihydro-purine-2,6-dione or a pharmaceutically acceptable salt thereof.

11. A compound of claim 1 which is 3-butyl-1-(3-methyl-but-2-enyl)-7-(toluene-4-sulfonyl)-3,7-dihydro-purine-2,6-dione or a pharmaceutically acceptable salt thereof.

12. A compound of claim 1 which is 3-butyl-7-(3,4-dimethoxy-benzenesulfonyl)-1-(3-methyl-but-2-enyl)-3,7-dihydro-purine-2,6-dione or a pharmaceutically acceptable salt thereof.

13. A method of stimulating endogenous calcitonin expression in a patient suffering from a condition associated with bone loss comprising administering a therapeutically effective amount of a compound of Formula (I)

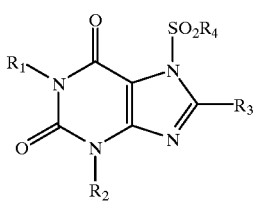

(I)

wherein:

$R_1$ and $R_2$ are independently, alkyl of 1 to 12 carbon atoms, alkenyl of 2 to 12 carbon atoms, allyl, substituted allyl of 3 to 12 carbon atoms, cycloalkyl of 3 to 10 carbon atoms, phenyl, naphthyl, 5 to 10 membered heteroaryl or a moiety of the formula $(CH_2)_m$—A wherein m is an integer from 1 to 9 and A is cycloalkyl of 3 to 7 carbon atoms;

$R_3$ is H, alkyl of 1 to 12 carbon atoms or cycloalkyl of 3 to 10 carbon atoms; and $R_4$ is alkyl of 1 to 12 carbon atoms, cycloalkyl of 3 to 10 carbon atoms, cycloalkylalkyl of 4 to 10 carbon atoms, phenyl, naphthyl, phenylalkyl wherein the alkyl group has from 1 to 4 carbon atoms; or 5 to 10 membered heteroaryl having 1 to 3 heteroatoms selected from N, S and O;

or a pharmaceutically acceptable salt thereof.

14. The method of claim 13 where the condition associated with bone loss is Paget's Disease, post menopausal osteoporosis, senile osteoporosis or glucocorticoid-induced osteoporosis.

* * * * *